(12) United States Patent
Kamiguchi

(10) Patent No.: US 10,566,102 B2
(45) Date of Patent: Feb. 18, 2020

(54) CHARGED PARTICLE BEAM THERAPY APPARATUS AND RIDGE FILTER

(71) Applicant: SUMITOMO HEAVY INDUSTRIES, LTD., Tokyo (JP)

(72) Inventor: Nagaaki Kamiguchi, Kanagawa (JP)

(73) Assignee: SUMITOMO HEAVY INDUSTRIES, LTD., Tokyo (JP)

( * ) Notice: Subject to any disclaimer, the term of this patent is extended or adjusted under 35 U.S.C. 154(b) by 262 days.

(21) Appl. No.: 15/691,323

(22) Filed: Aug. 30, 2017

(65) Prior Publication Data

US 2018/0068753 A1    Mar. 8, 2018

(30) Foreign Application Priority Data

Sep. 2, 2016 (JP) .................................. 2016-171800

(51) Int. Cl.
| | | |
|---|---|---|
| *G21K 1/10* | (2006.01) | |
| *A61N 5/10* | (2006.01) | |
| *G21K 5/04* | (2006.01) | |

(52) U.S. Cl.
CPC .............. *G21K 1/10* (2013.01); *A61N 5/1042* (2013.01); *A61N 5/1077* (2013.01); *A61N 2005/1087* (2013.01); *A61N 2005/1095* (2013.01); *G21K 5/04* (2013.01)

(58) Field of Classification Search
CPC .......... A61N 5/1077; A61N 2005/1095; A61N 2005/1087; A61N 5/1042; G21K 1/10
See application file for complete search history.

(56) References Cited

U.S. PATENT DOCUMENTS

2006/0226372 A1* 10/2006 Yanagisawa ............. A61N 5/10
                                                           250/396 R
2011/0012028 A1*  1/2011 Harada ................ A61N 5/1075
                                                           250/492.1

FOREIGN PATENT DOCUMENTS

| JP | 2012-231983 A | 11/2012 |
| JP | 2015-116284 A |  6/2015 |

\* cited by examiner

*Primary Examiner* — Christine H Matthews
*Assistant Examiner* — Joshua Daryl D Lannu
(74) *Attorney, Agent, or Firm* — Michael Best & Friedrich LLP

(57) ABSTRACT

A charged particle beam therapy apparatus includes an accelerator accelerating a charged particle and emitting a charged particle beam, an irradiation unit irradiating an irradiation subject with the charged particle beam, and a ridge filter provided in the irradiation unit and generating a spread out Bragg peak of the charged particle beam. The ridge filter includes multiple damping members reducing energy of the incident charged particle beam, in an intersecting direction intersecting an irradiating direction of the charged particle beam. The damping member has a cross-sectional area changing along the irradiating direction and has a side surface of when being seen in the intersecting direction, being bonded to a side surface of another damping member. A pass-through portion passing through the ridge filter in the irradiating direction is formed at a position different from a position of the damping member of when being seen in the irradiating direction.

3 Claims, 10 Drawing Sheets

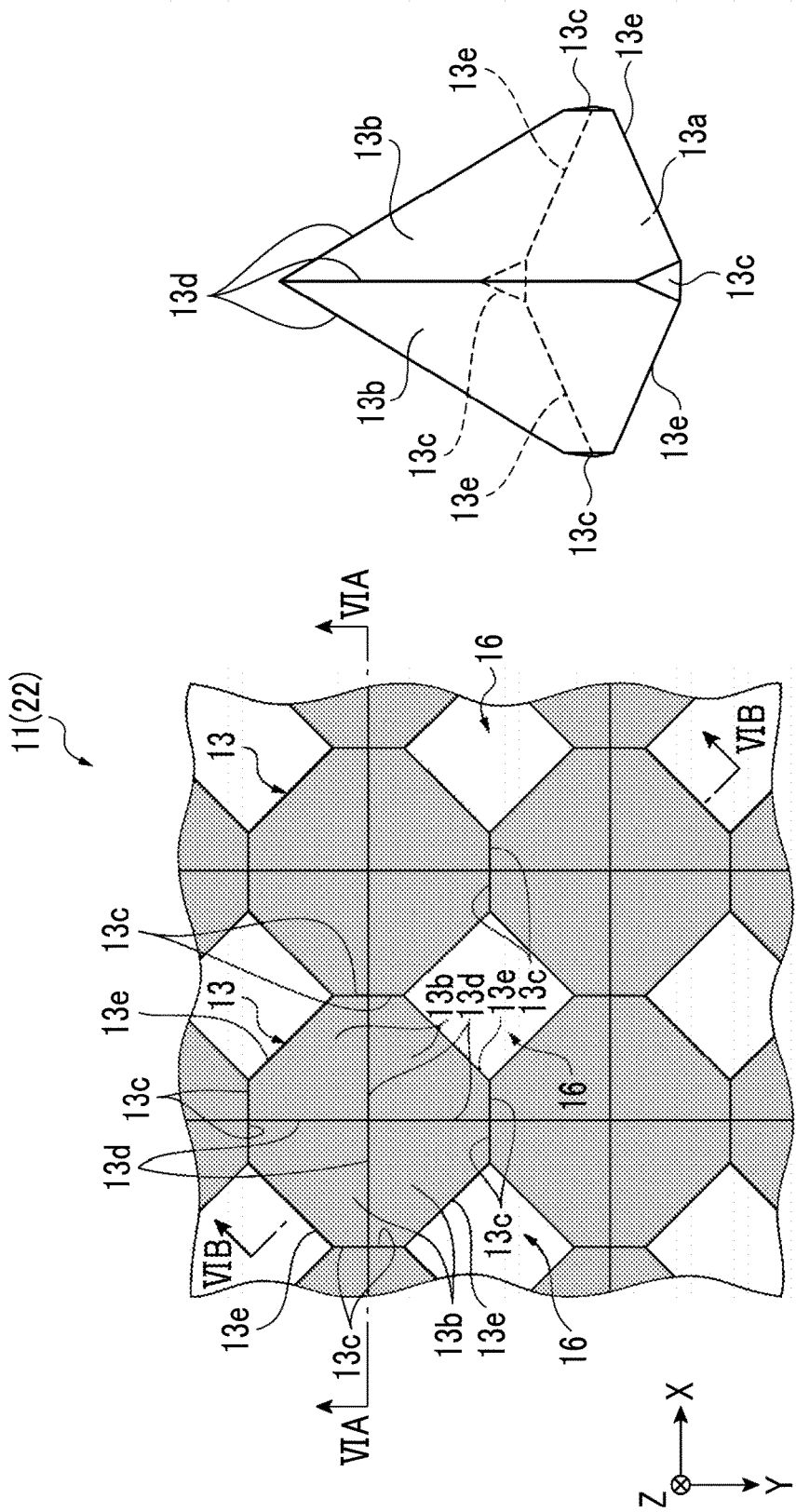

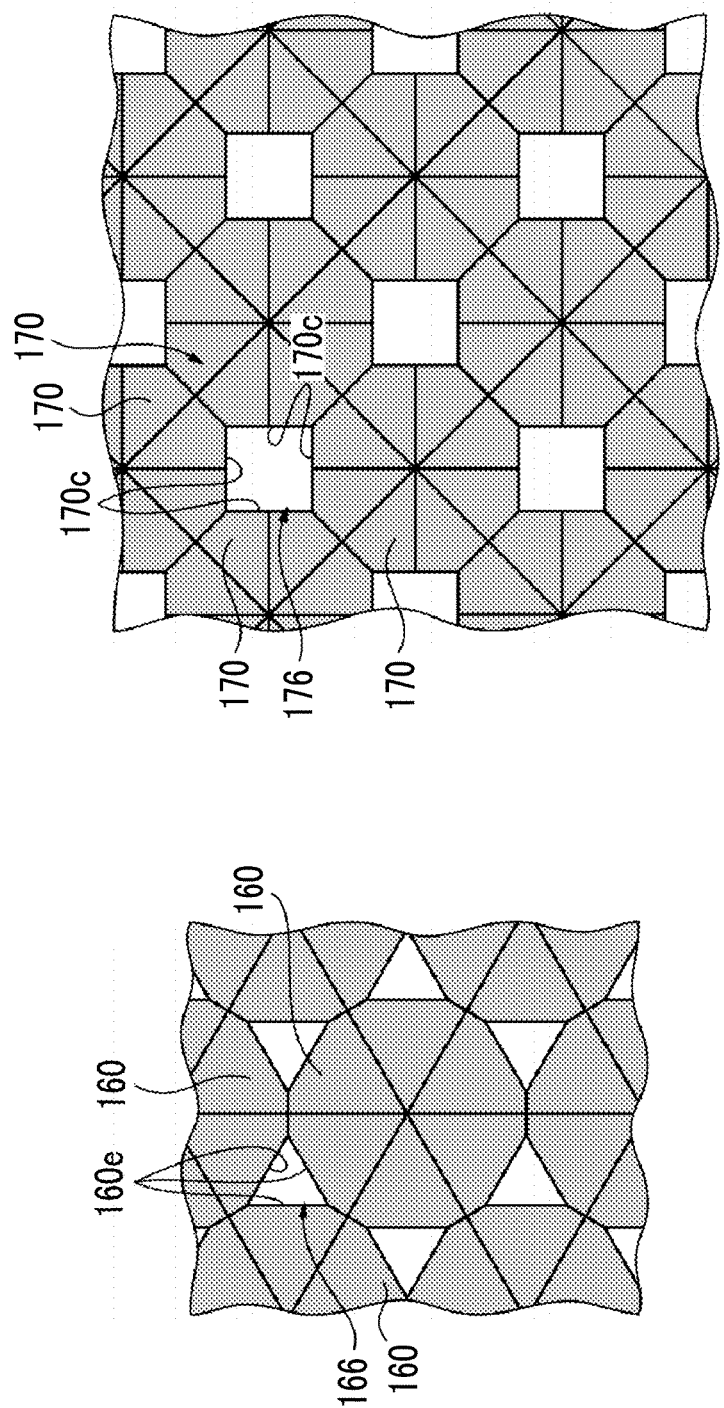

CHARGED PARTICLE BEAM THERAPY APPARATUS AND RIDGE FILTER

RELATED APPLICATIONS

Priority is claimed to Japanese Patent Application No. 2016-171800, filed Sep. 2, 2016, the entire content of which is incorporated herein by reference.

BACKGROUND

Technical Field

A certain embodiment of the present invention relates to a charged particle beam therapy apparatus and a ridge filter.

Description of Related Art

Charged particle beam therapy apparatuses performing irradiation of a charged particle beam are known. There are cases where such a charged particle beam therapy apparatus has a ridge filter for generating a spread out Bragg peak of the charged particle beam (for example, refer to the related art). The ridge filter has a plurality of damping portions which are extended and individually have a triangular cross-sectional shape. A support section lying throughout the whole region of the ridge filter supports a bottom portion side of the plurality of damping portions. Energy of charged particles configuring a charged particle beam is degraded in accordance with the thickness of the damping portion to passthrough. Therefore, in an irradiating direction of the charged particle beam, the energy of charged particles passing through a thick part of the damping portion is low, and the energy of charged particles passing through a thin part of the damping portion remains high. As a result, it is possible to obtain a charged particle beam in which charged particles having different energy are mixed together, that is, a charged particle beam having energy within a certain degree of width (having a spread out Bragg peak).

SUMMARY

According to an aspect of the present invention, there is provided a charged particle beam therapy apparatus including an accelerator configured to accelerate a charged particle and to emit a charged particle beam, an irradiation unit configured to irradiate an irradiation subject with the charged particle beam, and a ridge filter that is provided in the irradiation unit and generates a spread out Bragg peak of the charged particle beam. The ridge filter includes a plurality of damping members reducing energy of the incident charged particle beam, in an intersecting direction which intersects an irradiating direction of the charged particle beam. The damping member has a cross-sectional area changing along the irradiating direction and has a side surface in a case of being seen in the intersecting direction, being bonded to a side surface of another damping member. A pass-through portion passing through the ridge filter in the irradiating direction is formed at a position different from a position of the damping member in a case of being seen in the irradiating direction.

According to another aspect of the present invention, there is provided a ridge filter for a charged particle beam therapy apparatus generating a spread out Bragg peak of a charged particle beam. The ridge filter includes a plurality of damping members reducing energy of an incident charged particle beam in an intersecting direction which intersects an irradiating direction of the charged particle beam. The damping member has a cross-sectional area changing along the irradiating direction and has a side surface in a case of being seen in the intersecting direction, being bonded to a side surface of another damping member. A pass-through portion passing through the ridge filter in the irradiating direction is formed at a position different from a position of the damping member in a case of being seen in the irradiating direction.

BRIEF DESCRIPTION OF THE DRAWINGS

FIG. 5A is an enlarged view of the ridge filter, and FIG. 5B is a perspective view of damping members configuring the ridge filter.

FIGS. 9A and 9B are views illustrating a ridge filter according to an alternative modification example.

DETAILED DESCRIPTION

In a charged particle beam therapy apparatus of the related art, when a charged particle beam is incident on a ridge filter, the charged particle beam is incident not only on a damping portion but also on a support member. Therefore, there may be a disadvantage in that the charged particle beam scatters when the charged particle beam passes through the support member. If the charged particle beam scatters unexpectedly, there is a possibility that desired dose distribution of the charged particle beam will not be able to be obtained.

It is desirable to provide a charged particle beam therapy apparatus in which a charged particle beam can be restrained from scattering, and a ridge filter.

In a charged particle beam therapy apparatus according to an embodiment of the present invention, the ridge filter may include a plurality of damping members reducing energy of an incident charged particle beam, in an intersecting direction which intersects an irradiating direction of the charged particle beam. Here, the damping member may have aside surface in a case of being seen in the intersecting direction, being bonded to a side surface of another damping member. In this manner, when the adjacent damping members support each other, even if there is provided no support member supporting all the damping members, it is possible to ensure the strength for serving as the ridge filter. Since the strength can be ensured even if there is provided no support member, it is possible to form a pass-through portion which passes through the ridge filter in the irradiating direction at a position different from a position of the damping member in a case of being seen in the irradiating direction. According to such a structure, a charged particle beam which is not incident on the damping member can pass through the pass-through portion, and thus, the charged particle beam can travel to the downstream side of the ridge filter without scattering. Consequently, the charged particle beam can be restrained from scattering.

Figure 7B:
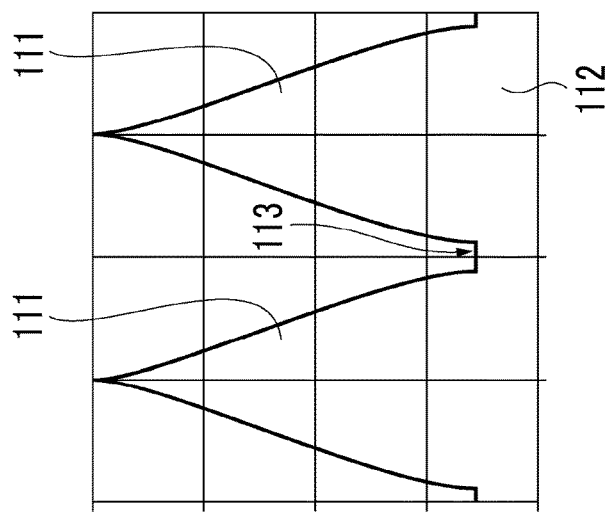
FIG. 7B is an enlarged cross-sectional view of the ridge filter according to the comparative example.
Figure 7A:
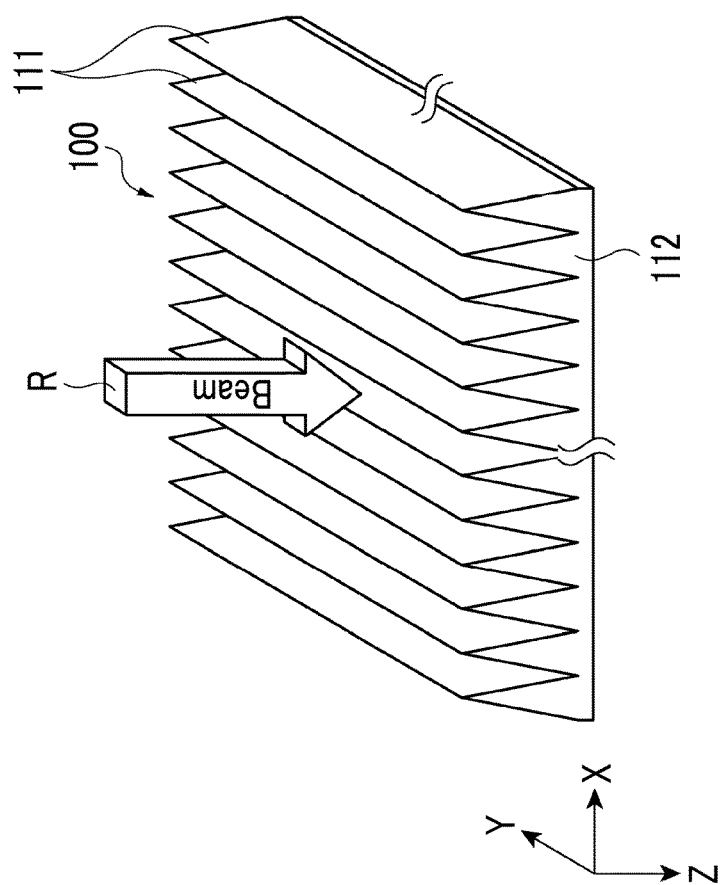
FIG. 7A is a perspective view illustrating the overall configuration of a ridge filter according to a comparative example.

In the charged particle beam therapy apparatus according to the embodiment of the present invention, the intersecting direction may have a first direction and a second direction which intersects the first direction. The damping members may individually have a pyramid shape, may be arranged along the first direction, and may be arranged along the second direction. According to such a configuration, even if there is provided no support member, it is possible to ensure the strength for serving as the ridge filter. In addition, since the damping members individually have a pyramid shape and are arranged along the first direction and the second direction, the damping members are disposed in a two-dimensional array. For example, in a ridge filter according to a comparative example as illustrated in FIGS. 7A and 7B, the damping members extending straight in the second direction are arranged in the first direction. Accordingly, there appears shade of a Bragg peak in the first direction, and there appears no shade in the second direction, resulting in shade having a striped pattern in a case of being seen in a planar manner. Meanwhile, since the damping members are disposed in a two-dimensional array, it is possible to obtain planar shade of the Bragg peak, so that the approximately even shade of the Bragg peak can be realized.

According to the ridge filter of the embodiment of the present invention, it is possible to obtain an operation and an effect similar to those of the charged particle beam therapy apparatus.

According to the embodiment of the present invention, the charged particle beam can be restrained from scattering.

Hereinafter, with reference to the accompanying drawings, a charged particle beam therapy apparatus and a ridge filter according to an embodiment of the present invention will be described. In the descriptions of the drawings, the same reference sign will be applied to the same element, and the description thereof will not be repeated.

Figure 1:
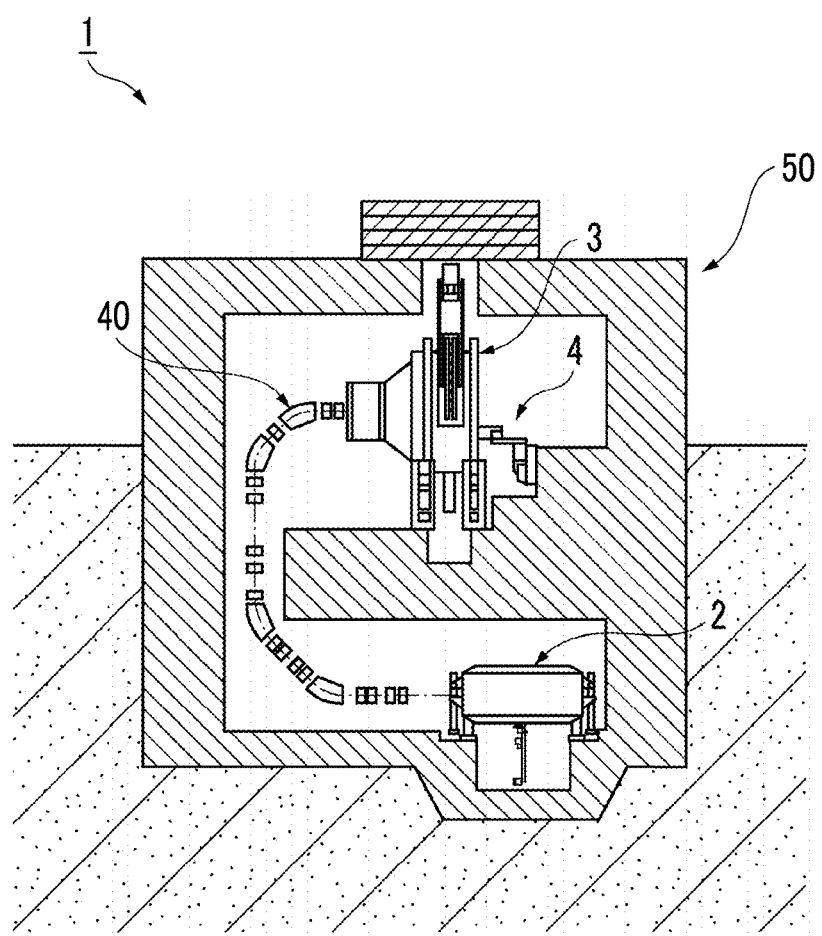
FIG. 1 is a sectional view of a structure in which a charged particle beam therapy apparatus according to an embodiment of the present invention is installed.
Figure 2:
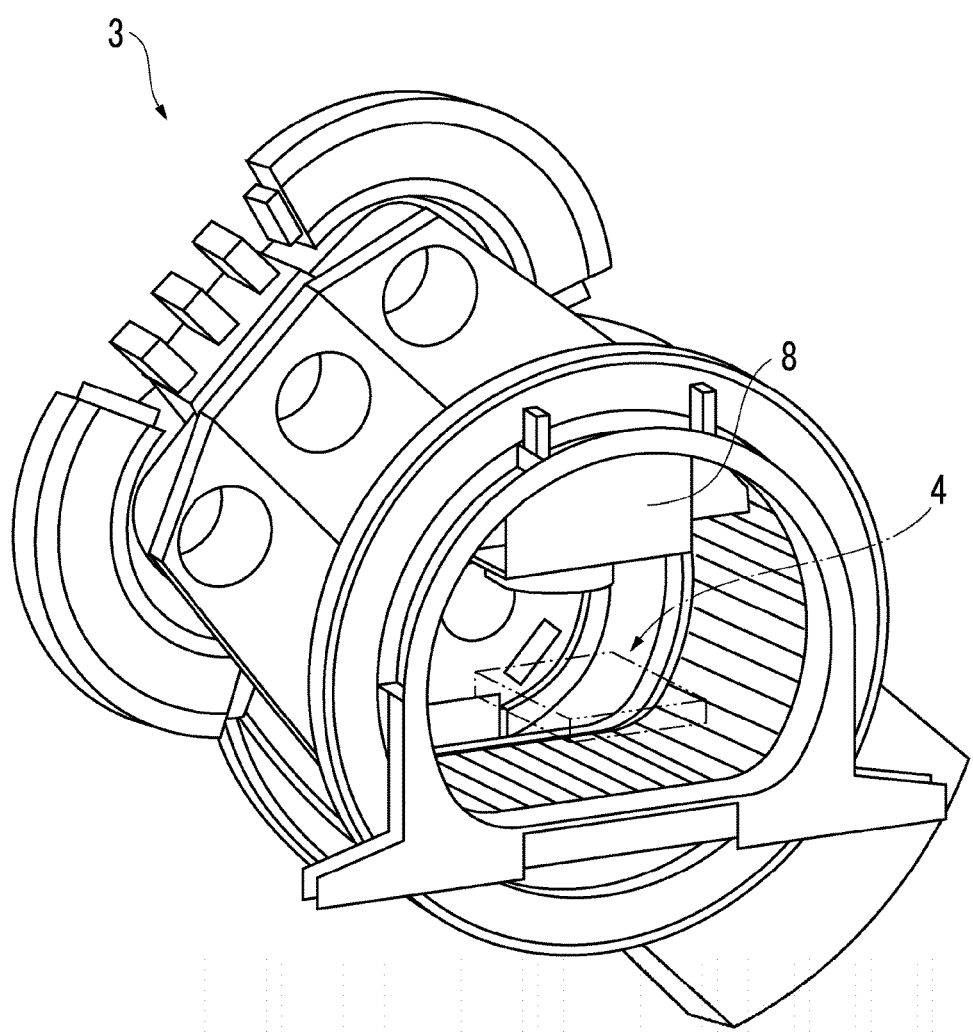
FIG. 2 is a perspective view illustrating a configuration in the vicinity of an irradiation unit of the charged particle beam therapy apparatus according to the embodiment of the present invention.
Figure 3:
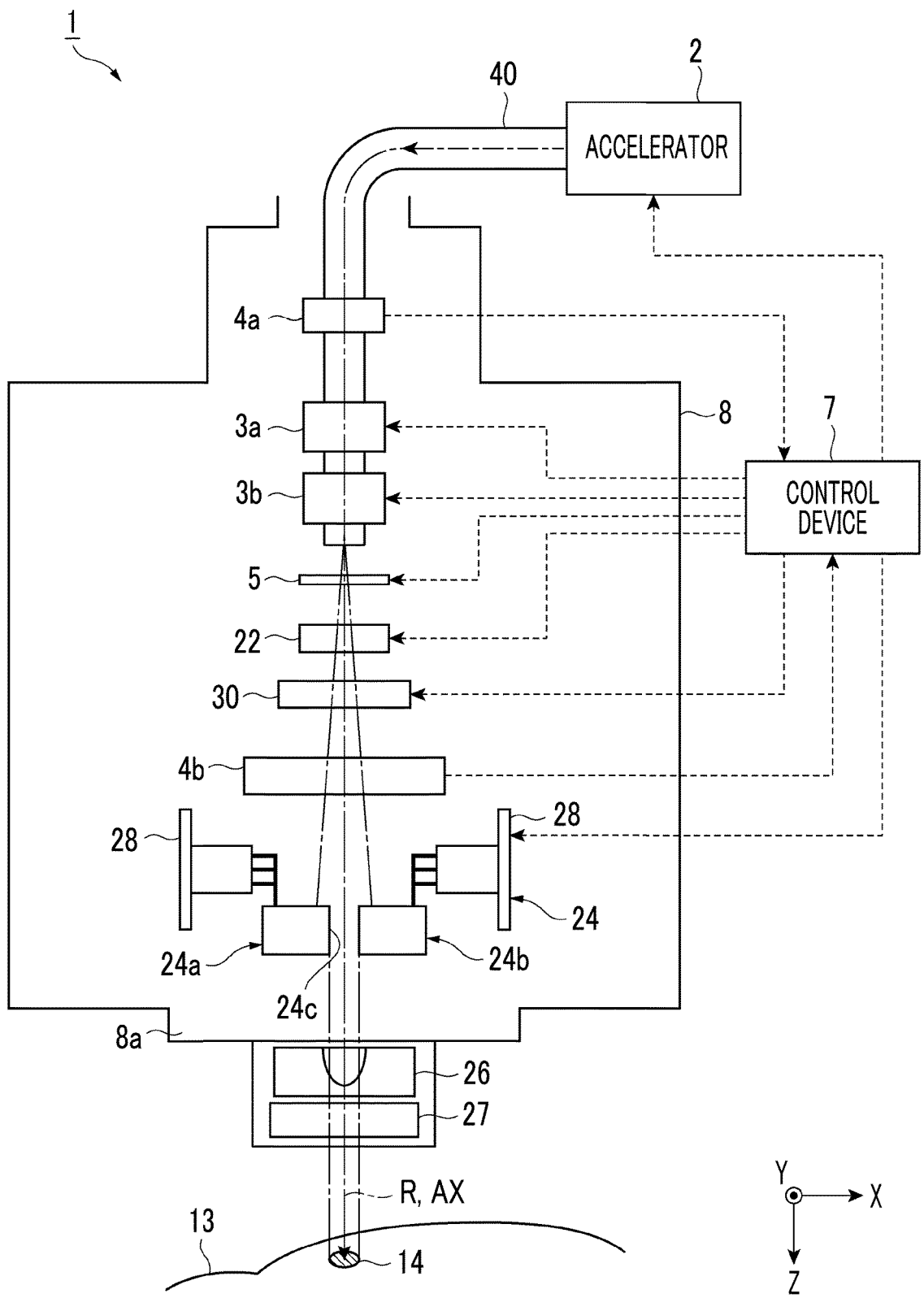
FIG. 3 is a schematic diagram of a configuration of the charged particle beam therapy apparatus according to the embodiment of the present invention.

FIG. 1 is a sectional view of a structure 50 in which the charged particle beam therapy apparatus according to the embodiment of the present invention is installed. FIG. 2 is a perspective view illustrating a configuration in the vicinity of an irradiation unit of the charged particle beam therapy apparatus according to the embodiment of the present invention. FIG. 3 is a schematic diagram of a configuration of the charged particle beam therapy apparatus according to the embodiment of the present invention. As illustrated in FIG. 3, a charged particle beam therapy apparatus 1 irradiates a tumor (irradiation subject) 14 inside the body of a patient 15 with a charged particle beam R. The charged particle beam R is realized by accelerating electrically charged particles at a high speed. Examples of the charged particle beam R include a proton beam, a heavy particle (heavy ion) beam, and a particle beam.

Hereinafter, descriptions will be given by using the terms of "X-axis direction", "Y-axis direction", and "Z-axis direction". The "Z-axis direction" is a direction in which a base axis AX of the charged particle beam R extends inside an irradiation unit 8 (will be described below in detail). The "base axis AX" is an irradiation axis of the charged particle beam R in a case where the charged particle beam R is not deflected due to scanning electromagnets 3a and 3b (will be described below). FIG. 3 illustrates a state where irradiation is performed with the charged particle beam R along the base axis AX. In the descriptions below, a direction in which irradiation is performed with the charged particle beam R along the base axis AX will be considered as "irradiating direction of the charged particle beam R". The "X-axis direction" is a direction within a plane orthogonal to the Z-axis direction. The "Y-axis direction" is a direction orthogonal to the X-axis direction within a plane orthogonal to the Z-axis direction.

As illustrated in FIGS. 1 and 3, the charged particle beam therapy apparatus 1 includes an accelerator 2, a rotary gantry 3 including the irradiation unit (irradiation nozzle) 8, a transportation line 40, and a control device 7. As illustrated in FIG. 1, the charged particle beam therapy apparatus 1 is installed in the structure 50. In the example illustrated in FIG. 1, the structure 50 is a multi-story building (here, a two-story building). The accelerator 2 and the rotary gantry 3 are respectively installed in rooms on each floor. The transportation line 40 is provided across the floors of the structure 50 and connects the accelerator 2 and the irradiation unit 8 of the rotary gantry 3 to each other (refer to FIG. 2). The rotary gantry 3 can rotate or oscillate around a treatment bed 4 on which the patient 15 is placed. The irradiating direction of a charged particle beam emitted by the irradiation unit 8 can be changed by rotating the rotary gantry 3. The accelerator 2 and the rotary gantry 3 may be installed on the same floor instead of being installed on floors different from each other. In addition, the irradiation unit 8 may be in a fixed state inside a room (so-called fixed irradiation method) instead of being attached to the rotary gantry 3.

The accelerator 2 accelerates charged particles and emits the charged particle beam R. Examples of the accelerator 2 include a cyclotron, a synchrotron, a cyclo-synchrotron, and a linear accelerator. The charged particle beam R generated by the accelerator 2 is transported to the irradiation unit 8 through the transportation line 40. The accelerator 2 is connected to the control device 7, and the control device 7 controls the operation of the accelerator 2.

The transportation line 40 is a line for transporting the charged particle beam R, which is emitted from the accelerator 2, to the irradiation unit 8. The transportation line 40 is provided with a duct of which the inside is in a vacuum state or filled with inert gas, a deflected electromagnet which generates a magnetic field for changing the traveling direction of the charged particle beam R passing through the inside of the duct, and the like.

The irradiation unit 8 irradiates the patient 15 placed on the treatment bed 4 inside the rotary gantry 3, with the charged particle beam R. The irradiation unit 8 includes the scanning electromagnets 3a and 3b, monitors 4a and 4b, a scatterer 5, a ridge filter 22, a degrader 30, a multi leaf collimator 24, a bolus 26, and a patient collimator 27. Each of components inside the irradiation unit 8 may be suitably omitted or may retreat to a position where irradiation of the charged particle beam R is not hindered, in accordance with the irradiation method of the charged particle beam R. In addition, the degrader 30 and the patient collimator 27 may be omitted.

A pair of electromagnets configures the scanning electromagnets 3a and 3b. A magnetic field between the pair of electromagnets is changed in response to a current supplied from the control device 7, and scanning is performed with the charged particle beam R passing through between the electromagnets. The X-axis directional scanning electromagnet 3a performs scanning with the charged particle beam R in the X-axis direction, and the Y-axis directional scanning electromagnet 3b performs scanning with the charged particle beam R in the Y-axis direction. The scanning electromagnets 3a and 3b are disposed on the base axis AX, that is, in order toward the downstream side of the accelerator 2. The scanning electromagnets 3a and 3b perform scanning with the charged particle beam R such that the charged particle beam R is on a trajectory set in advance (for example, a circular trajectory and a zig-zag trajectory).

The monitor 4a monitors the beam position of the charged particle beam R, and the monitor 4b monitors the absolute value of the dose of the charged particle beam R and dose distribution of the charged particle beam R. Each of the monitors 4a and 4b outputs monitored information obtained through the monitoring, to the control device 7. The monitor 4a is disposed on the base axis AX of the charged particle beam R, that is, on the downstream side of the accelerator 2 and on the upstream side of the X-axis directional scanning electromagnet 3a. The monitor 4b is disposed on the base axis AX, that is, on the downstream side of the degrader 30. However, the position of each of the monitors 4a and 4b is not particularly limited.

The scatterer 5 causes the charged particle beam R passing through the scatterer 5 to be diffused as a wide beam having a width in a direction orthogonal to the irradiation axis. The scatterer 5 has a plate shape and is formed of tungsten having a thickness of several millimeters, for example. On the base axis AX, the scatterer 5 is disposed on the downstream side of the scanning electromagnet 3b and on the upstream side of the monitor 4b.

The ridge filter 22 adjusts the dose distribution of the charged particle beam R. Specifically, the ridge filter 22 applies a spread out Bragg peak (SOBP) to the charged particle beam R such that the spread out Bragg peak copes with the thickness of the tumor 14 (length in the irradiating direction) inside the body of the patient 15. Accordingly, a Bragg peak of the charged particle beam R spreads evenly in the thickness direction (here, the Z-axis direction). The ridge filter 22 is disposed on the downstream side of the scatterer 5 and on the upstream side of the monitor 4b, on the base axis AX. The ridge filter 22 will be described below in detail.

The degrader 30 is disposed between the ridge filter 22 and the monitor 4b on the base axis AX. The degrader 30 degrades the energy of the charged particle beam R passing through the degrader 30 and adjusts the range of the charged particle beam R. In regards to the adjustment of the range, a rough adjustment may be performed by a degrader (not illustrated) provided immediately behind the accelerator 2, and a fine adjustment may be performed by the degrader 30 inside the irradiation unit 8. The degrader 30 is provided on the base axis AX, that is, on the downstream side in the charged particle beam R beyond the scanning electromagnets 3a and 3b, the scatterer 5, and the ridge filter 22. The degrader 30 adjusts the maximum arrival depth of the charged particle beam R inside the body of the patient 15. However, the position of the degrader 30 is not particularly limited. The degrader 30 is a plate-shaped member which spreads in the X-axis direction and the Y-axis direction.

The multi leaf collimator (hereinafter, will be referred to as "MLC") 24 forms a shape of the charged particle beam R (planar shape) in a plane direction perpendicular to the irradiating direction and has beam blocking portions 24a and 24b each including a plurality of teeth. The beam blocking portions 24a and 24b are disposed so as to face each other. An opening portion 24c is formed between the beam blocking portions 24a and 24b. The MLC 24 allows the charged particle beam R to pass through the opening portion 24c, thereby cutting out the charged particle beam R along a contour corresponding to the shape of the opening portion 24c.

In addition, the MLC 24 causes the beam blocking portions 24a and 24b to move forward and backward in a direction orthogonal to the Z-axis direction, thereby being capable of changing the position and the shape of the opening portion 24c. Moreover, the MLC 24 is guided by a linear guide 28 along the irradiating direction and can move along the Z-axis direction. The MLC 24 is disposed on the downstream side of the monitor 4b.

The bolus 26 forms a three-dimensional shape of a part of the charged particle beam R at the maximum arrival depth along the shape of a part of the tumor 14 at the maximum depth. For example, the shape of the bolus 26 is calculated based on the contour line of the tumor 14 and the electron density of surrounding tissue obtained from data of an X-ray CT. The bolus 26 is disposed on the downstream side of the MLC 24, on the base axis AX. The patient collimator 27 finally forms the planar shape of the charged particle beam R along the planar shape of the tumor 14. The patient collimator 27 may be disposed on the downstream side of the bolus 26, on the base axis AX, thereby being used as a substitute for the MLC 24, or both the MLC 24 and the patient collimator 27 may be used. The bolus 26 and the patient collimator 27 are provided at a tip portion 8a of the irradiation unit 8.

For example, the control device 7 is configured to include a CPU, a ROM, and a RAM. Based on the monitored information output from the monitors 4a and 4b, the control device 7 controls the operation of each of the accelerator 2, the scanning electromagnets 3a and 3b, the scatterer 5, the ridge filter 22, the degrader 30, and the MLC 24 as necessary.

In a case of performing irradiation of the charged particle beam R through a wobbler method (broad beam method) by using the charged particle beam therapy apparatus 1 illustrated in FIG. 3, the beam blocking portions 24a and 24b of the MLC 24 move forward and backward along the shape of the tumor 14, so that the opening portion 24c has a predetermined shape. In addition, the bolus 26 for the patient 15 to be treated and the patient collimator 27 are attached to the irradiation unit 8.

Subsequently, the charged particle beam R is emitted from the accelerator 2. The emitted charged particle beam R is used for performing scanning by the scanning electromagnets 3a and 3b so as to draw a predetermined trajectory and is diffused by the scatterer 5. Thereafter, the emitted charged particle beam R is formed and adjusted by the ridge filter 22, the degrader 30, the MLC 24, the bolus 26, and the patient collimator 27. Accordingly, the tumor 14 is irradiated with the charged particle beam R within an even irradiation range along the shape of the tumor 14.

FIG. 3 illustrates an example of the charged particle beam therapy apparatus 1 performed through the wobbler method. However, the charged particle beam therapy apparatus 1 may be configured to switch between the wobbler method and a different irradiation method (for example, layer stacking method) by switching the state of setting and retreatment of required configuration elements. In addition, since the ridge filter 22 according to the present embodiment can be used regardless of the irradiation method in a case of generating a spread out Bragg peak, the ridge filter 22 may be used when irradiation is performed through the layer stacking method. In a case of performing irradiation through the layer stacking method, a thin ridge filter 22 is used such that a spread out Bragg peak to be generated becomes smaller than a spread out Bragg peak at the time of the wobbler method (broad beam method).

Figure 4:
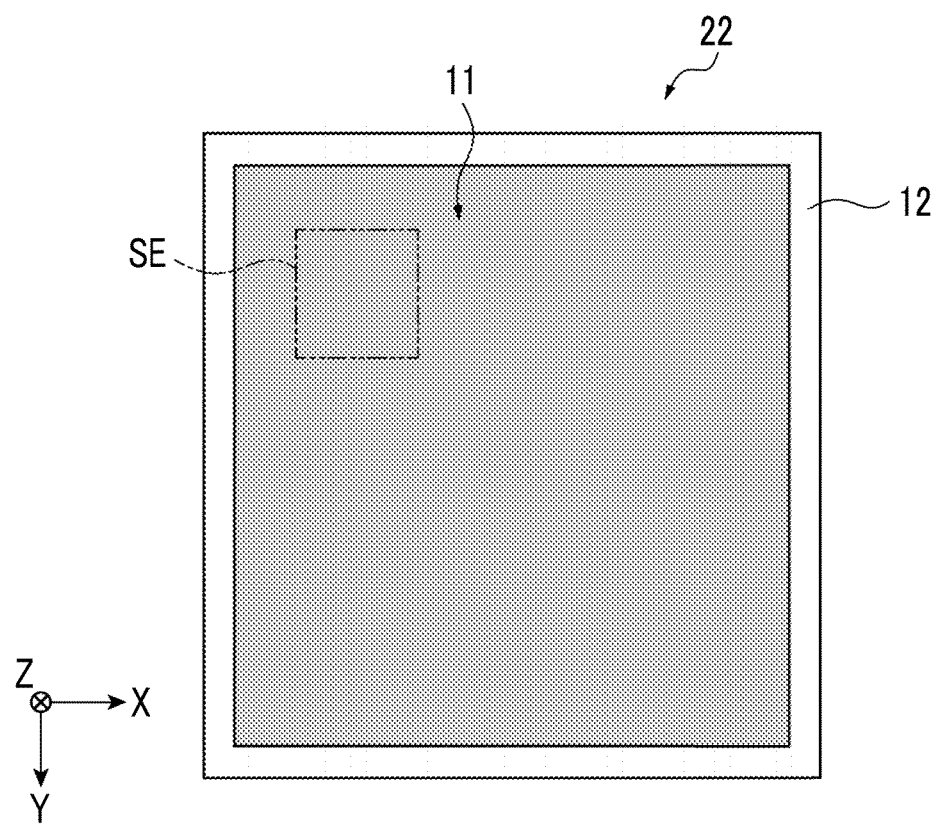
FIG. 4 is a view of a ridge filter seen from an upstream side toward a downstream side in an irradiating direction of a charged particle beam.
Figure 6A:
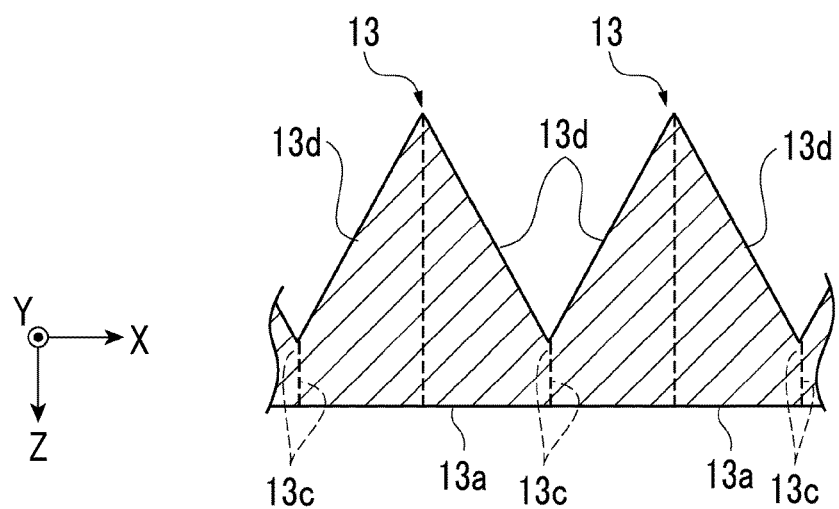
FIG. 6A is a cross-sectional view taken along line VIA-VIA illustrated in FIG. 5A.
Figure 6B:
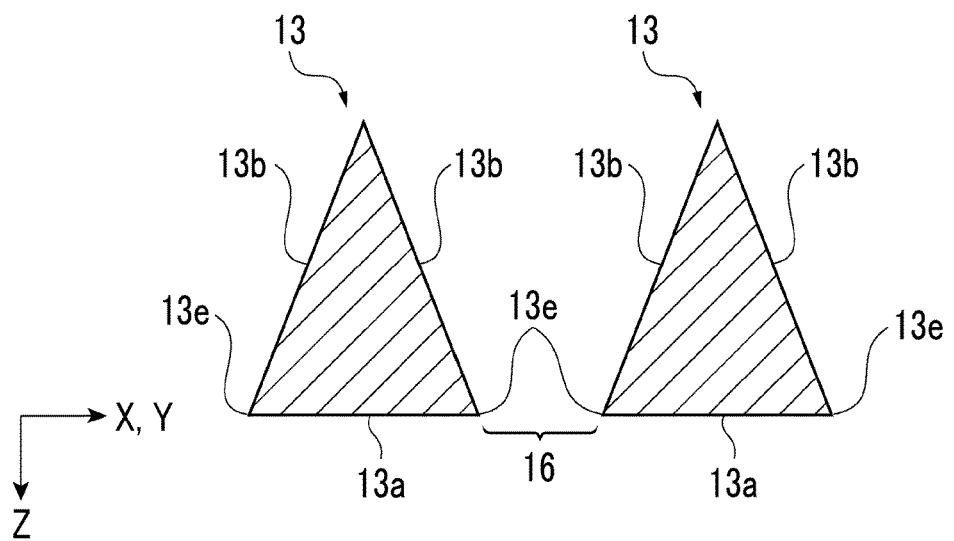
FIG. 6B is a cross-sectional view taken along line VIB-VIB illustrated in FIG. 5A.

Next, the configuration of the ridge filter 22 will be described in detail by using FIGS. 4 to 6. FIG. 4 is a view of a ridge filter seen from an upstream side toward a downstream side in an irradiating direction of a charged particle beam. FIG. 5A is an enlarged view of the ridge filter. FIG. 5B is an enlarged view of damping members configuring the ridge filter. FIG. 6A is a cross-sectional view taken along line VIA-VIA illustrated in FIG. 5A. FIG. 6B is a cross-sectional view taken along line VIB-VIB illustrated in FIG. 5A. In the description of the present embodiment, the XY-plane direction corresponds to "intersecting direction" in Claim, the X-axis direction corresponds to "first direction", and the Y-axis direction corresponds to "second direction". However, any positions in the XY-plane direction may respectively correspond to "the first direction" and "the second direction".

As illustrated in FIG. 4, the ridge filter 22 has a rectangular plate shape in its entirety and includes a main body portion 11 which is configured to have a rectangular plate shape, and frame bodies 12 which form a rectangular ring surrounding the main body portion 11 throughout the entire circumference. The frame bodies 12 are extended respectively along four sides of the main body portion 11 and are interlinked together at four corner portions of the main body portion 11. As described below, the main body portion 11 is a member having a plurality of pass-through portions 16. The frame body 12 can ensure the strength of the ridge filter 22 by supporting four sides of the main body portion 11. As the material of the ridge filter 22, for example, aluminum and resin may be used. The material of the main body portion 11 and the material of the frame body 12 may be the same as each other, or the materials may be different from each other. In a case of employing resin as the material of the ridge filter 22, it is possible to form a three-dimensional structure of the ridge filter 22 by using an optical shaping apparatus.

As illustrated in FIG. 5A, the main body portion 11 of the ridge filter 22 includes a plurality of damping members 13 reducing the energy of the incident charged particle beam R. The damping members 13 are arranged on the XY-plane which intersects the irradiating direction of the charged particle beam R (direction in which the base axis AX extends). The damping member 13 is a member of which a cross-sectional area changes along the irradiating direction of the charged particle beam R. In the present embodiment, as illustrated in FIG. 5B, the damping member 13 has a pyramid shape, that is, a quadrangular pyramid, of which the bottom surface is a substantial square (octagon of which four corners in the positive direction are chamfered), as a basic shape. Therefore, the cross-sectional area of the damping member 13 increases in the irradiating direction from the upstream side toward the downstream side (Z-axis positive direction). FIG. 5B is a perspective view illustrating the shape of each of the plurality of damping members 13 in the main body portion 11. As described below, as a surface bonded to another damping member 13, the damping member 13 has a side surface 13c on which a bottom surface 13a and two inclined surfaces 13b adjacent to each other are cut such that the corner portion is formed into a plane. The side surface 13c has a triangle shape. Here, the side surface 13c is defined for the convenience of description. However, in the actual ridge filter 22, since the damping members 13 are integrally bonded to each other, the boundary surface between the side surfaces 13c is in a vanished state.

As illustrated in FIG. 5A, in the present embodiment, one diagonal line on the bottom surface 13a of the damping member 13 is parallel to the Y-axis direction, the other diagonal line is disposed so as to be parallel to the X-axis direction. In such a state, the plurality of damping members 13 are arranged in the Y-axis direction, and the plurality thereof are arranged in the X-axis direction. That is, the damping members 13 are disposed in a two-dimensional manner along at least two directions. The damping member 13 has the side surfaces 13c on both end sides in the X-axis direction and has the side surfaces 13c on both end sides in the Y-axis direction. Therefore, the damping members 13 adjacent to each other in the X-axis direction are bonded to each other via the side surfaces 13c. The damping members 13 adjacent to each other in the Y-axis direction are bonded to each other via the side surfaces 13c. In addition, when the downstream side is seen from the upstream side in the irradiating direction, oblique sides 13d of each damping member 13 are interlinked with each other and are arranged so as to form a straight line extending straight in the Y-axis direction and a straight line extending straight in the X-axis direction.

According to such a configuration, the side surface 13c of the damping member 13 in a case of being seen in the XY-plane direction is bonded to the side surface 13c of another damping member 13. In the present embodiment, as illustrated in FIG. 6A, the side surface 13c of the damping member 13 in a case of being seen in the Y-axis direction is bonded to the side surface 13c of another damping member 13. In addition, on the upstream side in the irradiating direction (Z-axis directional negative side), the oblique sides 13d of each damping member 13 are combined, thereby realizing a configuration in which a plurality of protruding portions individually having an isosceles triangle shape are arranged (or a configuration in which a plurality of V-shaped groove portions are arranged). In addition, on the downstream side in the irradiating direction (Z-axis directional positive side), the bottom surfaces 13a of each damping member 13 are combined, thereby configuring a plane which spreads straight in the X-axis direction. Similarly, the side surface 13c of the damping member 13 in a case of being seen in the X-axis direction is bonded to the side surface 13c of another damping member 13. A cross-sectional shape in a case of being seen in the X-axis direction has the same conceptual configuration as a cross-sectional shape in a case of being seen in the Y-axis direction illustrated in FIG. 6A.

As illustrated in FIG. 5A, in the main body portion 11 of the ridge filter 22, at a position different from that of the damping member 13 in a case of being seen in the irradiating direction, the pass-through portion 16 passing through the main body portion 11 in the irradiating direction is formed. The position different from that of the damping member 13 denotes a region in the main body portion 11 excluding a region where the damping member 13 is disposed. That is, in the main body portion 11, the region where the damping member 13 is not disposed corresponds to "the position different from that of the damping member 13". In the present embodiment, the square pass-through portion 16 is formed at a part surrounded by edge portions 13e on the bottom surface 13a of each damping member 13. The pass-through portion 16 is formed such that diagonal lines are respectively parallel to the Y-axis direction and the X-axis direction. In addition, the plurality of pass-through portions 16 are arranged in the Y-axis direction at predetermined pitches and the plurality thereof are arranged in the X-axis direction at predetermined pitches.

The edge portion 13e of the damping member 13 in a case of being seen in the XY-plane direction is separated from the edge portion 13e of another damping member 13 via the pass-through portion 16. In the present embodiment, as illustrated in FIG. 6B, the edge portion 13e of the damping member 13 in a case of being seen in a direction oblique 45° to the Y-axis directional negative side toward the X-axis directional positive side is separated from the edge portion 13e of another damping member 13 via the pass-through portion 16. On the upstream side in the irradiating direction (Z-axis directional negative side), the inclined surfaces 13b of each damping member 13 are combined, thereby realizing a configuration in which a plurality of protruding portions individually having an isosceles triangle shape are arranged. In addition, on the downstream side in the irradiating direction (Z-axis directional positive side), while the bottom surface 13a of each damping member 13 is divided by the pass-through portion 16, a plane which spreads straight in the X-axis direction is configured. Similarly, the side surface 13c of the damping member 13 in a case of being seen in the X-axis direction is bonded to the side surface 13c of another damping member 13. A cross-sectional shape in a case of being seen in a direction oblique 45° to the Y-axis directional positive side toward the X-axis directional positive side has the same conceptual configuration as a cross-sectional shape illustrated in FIG. 6B.

The damping members 13 and the pass-through portions 16 are arranged so as to have the same shapes and to be in the same array in the entire region of the main body portion 11. In addition, the pattern structure formed by the damping members 13 and the pass-through portions 16 has symmetry with respect to the Y-axis and has symmetry with respect to the X-axis. Therefore, when being seen in the irradiating direction, in each of the regions in the main body portion 11, the ratio between an area occupied by the damping member 13 and an area occupied by the pass-through portion 16 becomes substantially uniform. Specifically, as illustrated in FIG. 4, a predetermined unit area SE is set with respect to the main body portion 11. Even in a case where the unit area SE is moved at random within the main body portion 11, the ratio between the area occupied by the damping member 13 and the area occupied by the pass-through portion 16 may be substantially uniform within the unit area SE. In a state where the ratio between the area occupied by the damping member 13 and the area occupied by the pass-through portion 16 is substantially uniform in such a manner, the strength of the main body portion 11 is ensured by causing the pyramid shapes to be interlinked with each other in a predetermined pattern in the Y-axis direction and the X-axis direction. Here, it is preferable that the main body portion 11 does not warp due to its own weight and the main body portion 11 maintains the strength to the extent that the posture of a flat plate shape can be maintained.

Next, the operation and the effect of the charged particle beam therapy apparatus 1 and the ridge filter 22 according to the present embodiment will be described.

First, with reference to FIGS. 7A and 7B, a ridge filter 100 according to a comparative example will be described. The ridge filter 100 according to the comparative example includes a plurality of damping members 111 which individually have the same cross-sectional shape and are arrayed in the X-axis direction, and a support member 112 which supports all the plurality of damping members 111. Each damping member 111 has a triangular cross-sectional shape protruding toward the upstream side in the irradiating direction of the charged particle beam R, and the cross-sectional shape extends along the Y-axis direction. In addition, as illustrated in FIG. 7B, a gap 113 is formed between the damping members 111 adjacent to each other. However, the support member 112 also spreads in a part corresponding to the gap 113. Therefore, the charged particle beam R incident on the ridge filter 100 passes through the support member 112 even in a place where the charged particle beam R does not pass through the damping member 111. Accordingly, there are cases where the charged particle beam R scatters due to the support member 112.

In contrast, in the charged particle beam therapy apparatus 1 according to the present embodiment, the ridge filter 22 includes the plurality of the damping members 13 reducing the energy of the incident charged particle beam R, in the XY-plane direction which intersects the irradiating direction of the charged particle beam R. Here, the side surface 13c of the damping member 13 in a case of being seen in the XY-plane direction is bonded to the side surface 13c of another damping member 13. In this manner, the damping members 13 adjacent to each other support each other, so that even if there is provided no support member supporting all the damping members 13, it is possible to ensure the strength for serving as the ridge filter 22. Furthermore, since the strength can be ensured even if there is provided no support member, it is possible to form the pass-through portion 16 which passes through the ridge filter 22 in the irradiating direction at a position different from that of the damping member 13 in a case of being seen in the irradiating direction. According to such a structure, a charged particle beam R which is not incident on the damping member 13 can pass through the pass-through portion 16, and thus, the charged particle beam R can travel to the downstream side of the ridge filter 22 without scattering. Consequently, the charged particle beam R can be restrained from scattering.

In the charged particle beam therapy apparatus 1 according to the present embodiment, the XY-plane direction has the X-axis direction and the Y-axis direction. The damping members 13 individually have a pyramid shape, are arranged along the X-axis direction, and are arranged along the Y-axis direction. According to such a configuration, even if there is provided no support member, it is possible to ensure the strength for serving as the ridge filter 22. In addition, since the damping members 13 individually have a pyramid shape and are arranged along the X-axis direction and the Y-axis direction, the damping members 13 are disposed in a two-dimensional array. For example, in the ridge filter 100 according to the comparative example as illustrated in FIGS. 7A and 7B, the damping members 111 extending straight in the Y-axis direction are arranged in the X-axis direction. Accordingly, there appears shade of a Bragg peak in the X-axis direction, and there appears no shade in the Y-axis direction, resulting in shade having a striped pattern in a case of being seen in a planar manner. Meanwhile, since the damping members 13 are disposed in a two-dimensional array, it is possible to obtain planar shade of the Bragg peak, so that the approximately even shade of the Bragg peak can be realized.

In addition, the ridge filter 22 according to the present embodiment is the ridge filter 22 for a charged particle beam therapy apparatus generating a spread out Bragg peak of the charged particle beam R. The ridge filter 22 includes the plurality of damping members 13 reducing the energy of the incident charged particle beam R in the XY-plane direction which intersects the irradiating direction of the charged particle beam R. The damping member 13 has a cross-sectional area changing along the irradiating direction and has the side surface 13c in a case of being seen in the intersecting direction, being bonded to the side surface 13c of another damping member 13. The pass-through portion 16 passing through the ridge filter 22 in the irradiating direction is formed at a position different from that of the damping member 13 in a case of being seen in the irradiating direction.

According to the ridge filter 22 of the present embodiment, it is possible to obtain an operation and an effect similar to those of the charged particle beam therapy apparatus 1.

The embodiment of the invention is not limited to the embodiment.

Figure 8A:
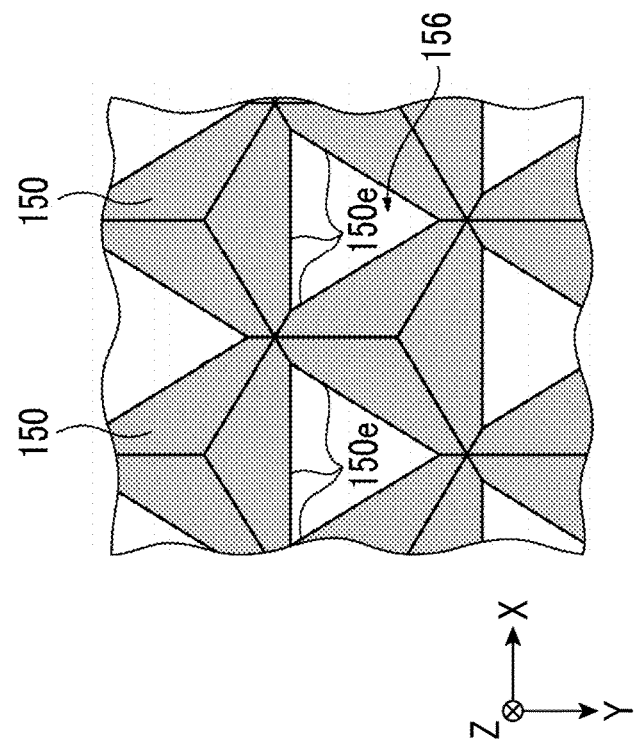
FIGS. 8A and 8B are views illustrating a ridge filter according to a modification example.
Figure 8B:
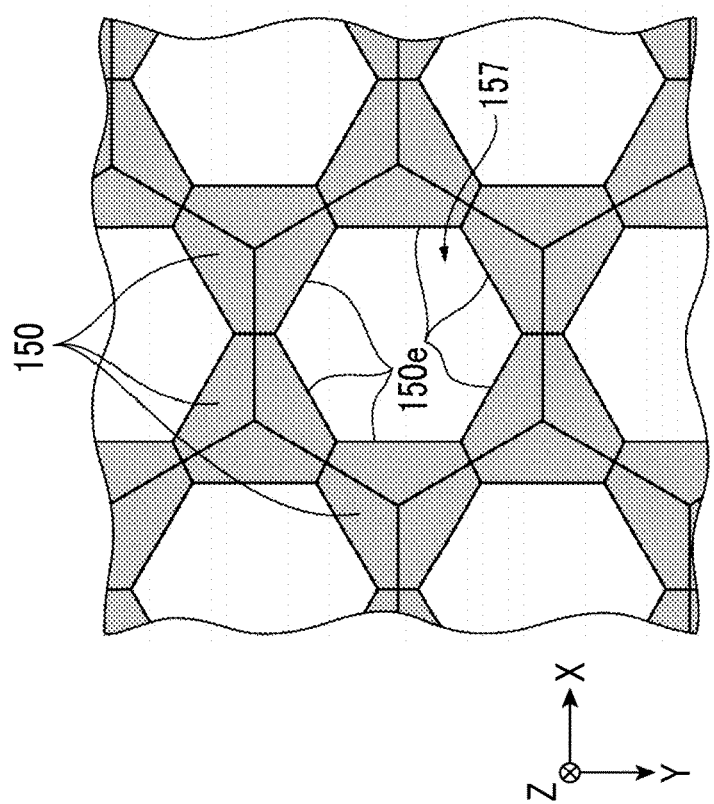

The shape and the array of the damping members are not limited to the embodiment. For example, as illustrated in FIGS. 8A and 8B, damping members 150 individually having a trigonal pyramid shape may be employed. In the example illustrated in FIG. 8A, the damping members 150 may be arranged in a state of being oriented toward a certain direction and may be arrayed in a pattern such that a triangular pass-through portion 156 is formed by edge portions 150e of three damping members 150. Alternatively, as illustrated in FIG. 8B, the damping members 150 may be arrayed in a pattern such that six damping members 150 are bonded to each other while varying the orientations and a hexagonal pass-through portion 157 is formed by the edge portion 150e of each damping member 150. In any of the examples in FIGS. 8A and 8B, the damping members 150 is bonded to an adjacent damping members 150 via a side surface formed in a part at a corner portion.

In addition, as illustrated in FIG. 9A, a damping member 160 having a hexagonal pyramid shape is employed and is bonded to another damping member 160 via a side surface at a corner portion. A triangular pass-through portion 166 is formed by edge portions 160e of the damping members 160. As illustrated in FIG. 9B, a damping member 170 having an octagonal pyramid shape is employed and is bonded to another damping member 170 via a side surface. A square pass-through portion 176 is formed by edge portions 170c of the damping members 170.

Figure 10:
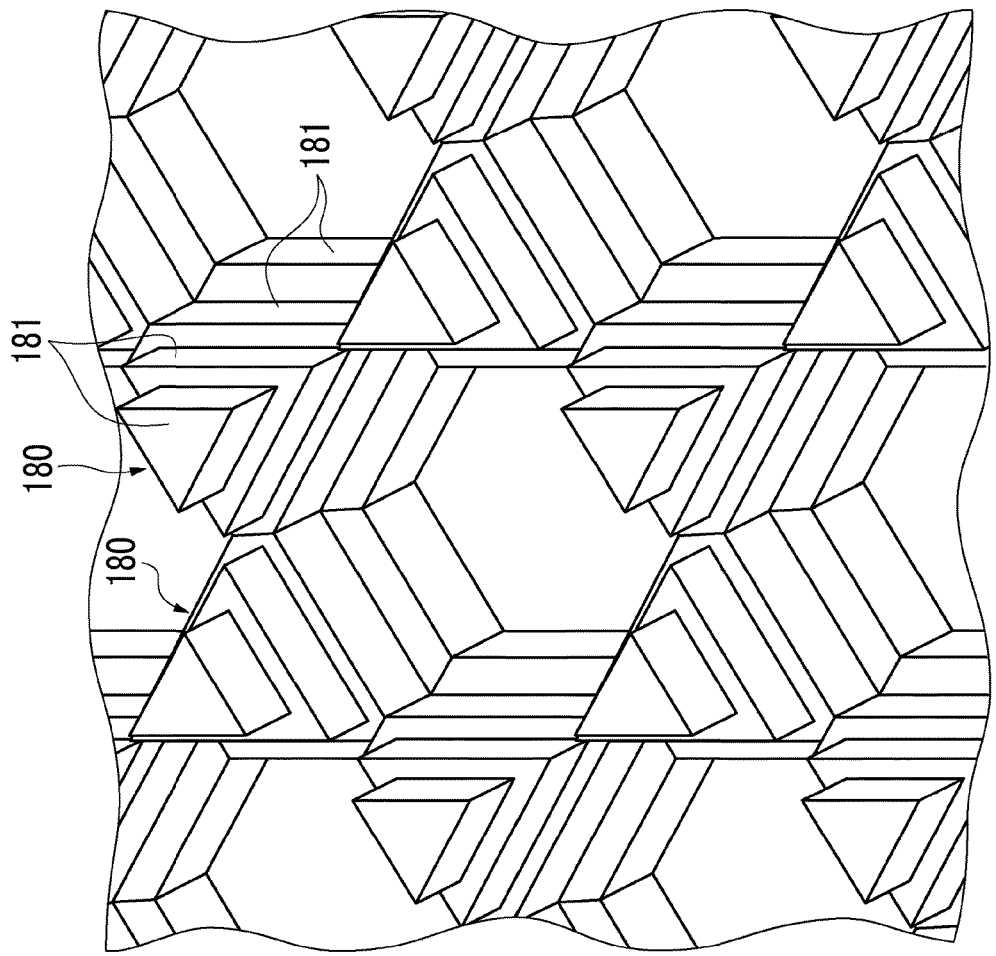
FIG. 10 is a perspective view illustrating the ridge filter according to the alternative modification example.

In addition, the damping member does not have to have a perfect pyramid shape as in the embodiment and modification examples. The damping member may be configured to have an approximated pyramid shape by combining stepped shapes. For example, a ridge filter illustrated in FIG. 10 includes damping members 180 configured to be approximated to the damping members 150 individually having a trigonal pyramid shape in the ridge filter illustrated in FIG. 8B. Each damping member 180 is configured to include a plurality of members 181 which individually have a substantially triangular plate shape and are stacked. The members 181 are gradually reduced in size toward the upstream side in the irradiating direction, while maintaining similar figures. Accordingly, the damping member 180 has a configuration in which the inclined surfaces of the trigonal pyramid are approximated with a plurality of stepped surfaces. Such a damping member 180 also corresponds to the shape of which the cross-sectional area changes along the irradiating direction.

In all the cases of FIGS. 8A, 8B, 9A, and 9B, the damping members are arrayed in a particular pattern along the X-axis direction and the Y-axis direction. Therefore, in each region of the ridge filter, the ratio between the area occupied by the damping member and the area occupied by the pass-through portion can be substantially uniform. In a case other than those of FIGS. 8A, 8B, 9A, and 9B, damping members having any shape and array pattern may be employed. The damping members of each the ridge filter form a geometric pattern which satisfies plane-filling of Archimedes. In addition, all the pyramid shapes of the damping members in the above-described examples may be replaced by cone shapes.

It should be understood that the invention is not limited to the above-described embodiment, but may be modified into various forms on the basis of the spirit of the invention. Additionally, the modifications are included in the scope of the invention.

What is claimed is:

1. A charged particle beam therapy apparatus comprising:
an accelerator configured to accelerate a charged particle and to emit a charged particle beam;
an irradiation unit configured to irradiate an irradiation subject with the charged particle beam; and
a ridge filter that is provided in the irradiation unit and generates a spread out Bragg peak of the charged particle beam,
wherein the ridge filter includes a damping member configured for reducing energy of the charged particle beam, in an intersecting direction which intersects an irradiating direction of the charged particle beam,
wherein the damping member includes a cross-sectional area changing along the irradiating direction and includes a side surface in a case of being seen in the intersecting direction, being bonded to a side surface of another damping member, and
wherein a pass-through portion passing through the ridge filter in the irradiating direction is formed at a position different from a position of the damping member in a case of being seen in the irradiating direction.

2. The charged particle beam therapy apparatus according to claim 1,
wherein the intersecting direction has a first direction and a second direction which intersects the first direction, and
wherein the damping member is one of a plurality of damping members which individually have a pyramid shape, are arranged along the first direction, and are arranged along the second direction.

3. A ridge filter for a charged particle beam therapy apparatus generating a spread out Bragg peak of a charged particle beam, the ridge filter comprising:
a damping member configured for reducing energy of an incident charged particle beam in an intersecting direction which intersects an irradiating direction of the charged particle beam,
wherein the damping member includes a cross-sectional area changing along the irradiating direction and includes a side surface in a case of being seen in the intersecting direction, being bonded to a side surface of another damping member, and
wherein a pass-through portion passing through the ridge filter in the irradiating direction is formed at a position different from a position of the damping member in a case of being seen in the irradiating direction.

* * * * *